United States Patent
Cowe et al.

(10) Patent No.: US 11,833,332 B2
(45) Date of Patent: Dec. 5, 2023

(54) MEDICAMENT PACKAGING ASSEMBLY

(71) Applicant: Owen Mumford Limited, Woodstock (GB)

(72) Inventors: Toby Cowe, Woodstock (GB); Timothy Evans, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 26 days.

(21) Appl. No.: 16/968,003

(22) PCT Filed: Feb. 6, 2019

(86) PCT No.: PCT/GB2019/050317
§ 371 (c)(1),
(2) Date: Aug. 6, 2020

(87) PCT Pub. No.: WO2019/155202
PCT Pub. Date: Aug. 15, 2019

(65) Prior Publication Data
US 2021/0379287 A1    Dec. 9, 2021

(30) Foreign Application Priority Data
Feb. 6, 2018   (GB) .................................... 1801895

(51) Int. Cl.
*A61M 5/24*    (2006.01)
*A61M 5/00*    (2006.01)
(Continued)

(52) U.S. Cl.
CPC .......... *A61M 5/2466* (2013.01); *A61M 5/002* (2013.01); *A61M 5/288* (2013.01);
(Continued)

(58) Field of Classification Search
CPC .... A61M 5/20; A61M 5/2033; A61M 5/2422; A61M 5/2429; A61M 5/2455;
(Continued)

(56) References Cited

U.S. PATENT DOCUMENTS

| 3,401,693 A | 9/1968 | Cohen |
| 5,250,037 A | 10/1993 | Bitdinger |

(Continued)

FOREIGN PATENT DOCUMENTS

| EP | 0239673 A2 | 10/1987 |
| EP | 0602883 A2 | 6/1994 |

(Continued)

OTHER PUBLICATIONS

International Search Report and Written Opinion of the International Searching Authority from corresponding PCT Application No. PCT/GB2019/050317, dated Jul. 2, 2019 (9 pages).

*Primary Examiner* — Jenna Zhang
(74) *Attorney, Agent, or Firm* — Quarles & Brady LLP (57) ABSTRACT

A medicament packaging assembly for installation in a medicament delivery device is disclosed. The packaging assembly comprises a cartridge having a medicament chamber, a sealing element for sealing a distal end of the medicament chamber, a sealing element release member, a cannula and a removable cap member. The assembly is switchable from a starting configuration in which the release member is spaced from the sealing element to an activated configuration in which the release member cooperates with the sealing element to connect the medicament chamber to the cannula. The packaging assembly further comprises a first chamber defined in part by the cap member and arranged for receiving the cannula such that at least a distal end of the cannula is sealed in the first chamber when the cap member is in place, and a second chamber defined in part by (Continued)

the sealing element and arranged for receiving the release member.

26 Claims, 9 Drawing Sheets

(51) Int. Cl.
*A61M 5/32* (2006.01)
*A61M 5/28* (2006.01)
*A61M 5/31* (2006.01)

(52) U.S. Cl.
CPC ..... *A61M 5/3202* (2013.01); *A61M 2005/247* (2013.01); *A61M 2005/312* (2013.01)

(58) Field of Classification Search
CPC .. A61M 5/2466; A61M 5/3202; A61M 5/002; A61M 5/326; A61M 5/288; A61M 2005/2006; A61M 2005/2026; A61M 2005/2073; A61M 2005/208; A61M 2005/2407; A61M 2005/247; A61M 2005/2474; A61M 2005/312; A61M 2005/3118

See application file for complete search history.

(56) References Cited

U.S. PATENT DOCUMENTS

| | | | |
|---|---|---|---|
| 7,559,919 B2* | 7/2009 | Pech | A61M 5/3213 604/192 |
| 11,273,264 B2* | 3/2022 | Okihara | A61M 5/5086 |
| 2008/0183140 A1 | 7/2008 | Paproski et al. | |
| 2009/0171311 A1 | 7/2009 | Genosar et al. | |
| 2013/0331796 A1* | 12/2013 | Wozencroft | A61M 5/3204 604/197 |
| 2018/0353704 A1* | 12/2018 | Helmer | A61M 5/2033 |
| 2018/0369497 A1* | 12/2018 | Schader | A61M 5/3204 |

FOREIGN PATENT DOCUMENTS

| | | | |
|---|---|---|---|
| GB | 1511259 A | 5/1978 | |
| WO | 2006058435 A2 | 6/2006 | |
| WO | WO-2017009640 A1 * | 1/2017 | ............... A61J 1/06 |

* cited by examiner

MEDICAMENT PACKAGING ASSEMBLY

CROSS-REFERENCE TO RELATED APPLICATIONS

This application represents the U.S. National Stage of International Application No. PCT/GB2019/050317 filed Feb. 6, 2019, which claims priority to British Patent Application Serial No. GB 1801895.2, filed Feb. 6, 2018, all of which are incorporated herein by reference in their entirety.

FIELD OF THE INVENTION

The present invention relates to packaging for medicaments. In particular, but not exclusively, the invention relates to a sterile packaging assembly that can be installed in a medicament delivery device.

BACKGROUND TO THE INVENTION

Medicaments for use in injection devices and auto-injectors are typically packaged in a pre-filled syringe having a staked needle, with the needle protected and kept sterile by a removable cap. The pre-filled syringe provides a sterile unit that remains aseptically sealed during installation in a device and during subsequent storage of the device. One disadvantage of this arrangement is that the injection devices must be configured to deliver the medicament through the staked needle of the pre-filled syringe, which may not always be the optimum choice since usually only a single type of primary package is available for a given medicament.

The present applicant's International Patent Application Publication No. WO 2017/009640 A1, the contents of which are hereby incorporated by reference, describes medicament packages in which the medicament is contained within a cartridge that is sealed with a sealing element in the form of a septum. The cartridges are arranged to engage with devices that include a release member that is arranged to pierce the septum when the cartridge is inserted into the device. This arrangement allows greater choice in the type of cannula used to deliver the medicament, whilst maintaining the advantages of a simple, universal primary package.

In some embodiments disclosed in WO 2017/009640 A1, the cartridge is arranged to engage with the device in two positions. In a first engagement position, the release member is spaced from the septum so that the medicament remains sealed in the cartridge. The device can be sold, transported and handled in this state. To prepare the device for delivery of the medicament, the cartridge is moved into a second engagement position relative to the device, in which the release member pierces the septum to allow the medicament to flow to the cannula.

In these cases, care must be taken to achieve and maintain the sterility of substantially the whole device before and during installation of the cartridge and during subsequent storage and transportation of the assembled device.

It is against that background that the present invention has been devised.

SUMMARY OF THE INVENTION

According to a first aspect of the invention, a medicament packaging assembly for installation in a medicament delivery device is provided. The packaging assembly comprises a cartridge having a medicament chamber for containing a medicament, a sealing element for sealing a distal end of the medicament chamber, a sealing element release member, a cannula for delivery of the medicament and a removable cap member. The assembly is switchable by relative movement between the release member and the cartridge from a starting configuration in which the release member is spaced from the sealing element to an activated configuration in which the release member cooperates with the sealing element to connect the medicament chamber to the cannula. The packaging assembly further comprises a first chamber defined in part by the cap member and arranged for receiving the cannula such that at least a distal end of the cannula is sealed in the first chamber when the cap member is in place, and a second chamber defined in part by the sealing element and arranged for receiving the release member such that at least a proximal end of the release member is sealed in the second chamber when the assembly is in the starting configuration. The assembly can be pre-assembled in the starting configuration for subsequent installation in the device.

Embodiments of the invention therefore provide a packaging assembly in which the medicament and all of the components that come into direct contact with the medicament can be sealed in sterile conditions for storage, transportation and handling of the packaging assembly and for subsequent installation of the packaging assembly in a delivery device in the same way as a pre-filled syringe, but without a permanent connection between the cannula and the medicament. Instead, the medicament is sealed in the medicament chamber and is only connected to the cannula when the assembly is switched to the activated configuration, reducing the risk of leakage and contamination. Furthermore, the type of cannula can be selected independently of the cartridge, increasing the flexibility of the arrangement.

The cap member may be arranged for engagement with an outer cap of the device. For example, the cap member may be arranged to engage with the outer cap of the device upon application of a distally-directed force to the assembly. The cap member may comprise one or more engagement formations for engagement with the outer cap. The or each engagement formation may be arranged to flex in order to engage the cap member with the outer cap. The or each engagement formation of the cap member may comprise a clip, a ramp formation, a projection, a recess, an aperture, a slot or any other suitable formation for engagement with a clip or other suitable complementary engagement formation of the outer cap.

Preferably, the cap member comprises at least one blocking formation for limiting relative movement between the release member and the cartridge in at least one direction, thereby to keep the assembly in the starting configuration when the cap member is in place. With this arrangement, the risk of accidental activation of the packaging assembly, for example due to mis-handling, is reduced.

When the cap member is arranged to engage with the outer cap of the device upon application of a distally-directed force to the assembly, the blocking formation is preferably arranged to keep the assembly in the starting configuration during application of the distally-directed force. In this way, the installation of the packaging assembly into a delivery device is simplified.

To allow the packaging assembly to be easily inserted into a device from a proximal end of the housing of the device, the cap member preferably has a diameter equal to or less than the diameter of the cartridge. The maximum diameter of the packaging assembly may be equal to the diameter of the cartridge.

The cap member may comprise a vent for venting the first chamber. The vent may comprise an air permeable sterile barrier material. In this way, the pressures in the first chamber and the second chamber can be equalised with atmospheric pressure outside the device, without compromising the sterility of the chambers. Advantageously, the presence of a vent eliminates pressure gradients across the seals that close the respective chambers, therefore reducing the risk of seal failure.

The packaging assembly may further comprise a hub subassembly including a hub body, the cannula and the release member. The packaging assembly may also comprise a coupling element attached to the cartridge, in which case the second chamber may be defined in part by the coupling element and an aseptic seal may be formed between the hub body and the coupling element to seal the second chamber at least when the assembly is in the starting configuration.

The packaging assembly may comprise a seal member arranged to provide the aseptic seal between the hub body and the coupling element.

Preferably, the hub body comprises a proximally-projecting boss for the release member and the second chamber is defined in part by a distally-projecting tubular member of the coupling element. With this arrangement, the tubular member may be arranged to receive the boss and the aseptic seal may be formed between the tubular member and the boss at least when the assembly is in the starting configuration.

When the aseptic seal is provided by a seal member, the seal member may comprise an elastomeric cap mounted on the boss. The release member may project through the elastomeric cap, and the elastomeric cap may form the aseptic seal between the tubular member and the boss. In another arrangement, the seal member comprises an elastomeric O-ring disposed between the tubular member and the boss.

The cap member is preferably engageable with the hub body and the or each blocking formation preferably extends proximally from the cap member to cooperate with the coupling element to limit relative movement between the release member and the cartridge. A tip of the or each blocking formation may be arranged to abut the coupling element to limit relative movement between the release member and the cartridge. The or each blocking formation may extend through a corresponding aperture in the hub body.

The coupling element may be attached to a collar of the cartridge by a crimp fitting. The coupling element may for example comprise a skirt that extends over the collar to form the crimp fitting.

The sealing element preferably comprises a septum, and the coupling element preferably clamps the septum against a distal end of the cartridge.

The packaging assembly may comprise a clip formation arranged to allow engagement of the hub subassembly with the coupling element during assembly of the packaging assembly and to prevent subsequent disengagement of the hub subassembly from the coupling element. For example, the hub body may comprise one or more inwardly-extending clips or barbs that cooperate with a collar of the coupling element to provide the clip formation.

The release member preferably comprises a tubular element arranged to pierce the sealing element upon switching of the assembly into the activated configuration. For example, the cannula may comprise a distal part of a needle and the release member may comprise a proximal part of the needle.

In a second aspect, the present invention resides in a method for assembling a medicament delivery device, comprising assembling a medicament packaging assembly according to the first aspect of the invention, and inserting the assembled packaging assembly into the medicament delivery device.

The method may further comprise engaging the cap member of the packaging assembly with an outer cap of the delivery device. For example, the step of inserting the packaging assembly may comprise applying a distally-directed force to the packaging assembly to engage the cap member with the outer cap.

In a third aspect of the present invention, a medicament delivery device is provided. The device comprises a housing for receiving a medicament packaging assembly according to the first aspect of the invention, and a removable outer cap provided on a distal end of the housing, the outer cap being engageable with the cap member of the packaging assembly when the packaging assembly is inserted into the housing.

The outer cap and/or the cap member may comprise one or more engagement formations arranged to couple the outer cap and the cap member together when the packaging assembly is inserted into the housing. At least one of the engagement formations may be arranged to flex in order to engage the cap member with the outer cap. The or each engagement formation of either the cap member or the outer cap may comprise a clip, a ramp formation, a projection, a recess, an aperture, a slot or any other suitable formation for engagement with a clip or other suitable complementary engagement formation of the other of the cap member and the outer cap.

The device may comprise an activation mechanism operable to cause relative movement between the cartridge and the hub subassembly, thereby to switch the packaging assembly from the starting configuration to the activated configuration to allow delivery of the medicament through the cannula.

A fourth aspect of the invention resides in a cannula module for use in a packaging assembly in which a medicament is contained in a medicament chamber of a cartridge. The cannula module comprises a sealing element for sealing an end of the medicament chamber, a coupling element, a cap sleeve member and a hub subassembly, the hub subassembly comprising a hub body, a cannula for delivery of the medicament and a sealing element release member. At least a distal end of the cannula is received in a first chamber defined in part by the cap member and in part by the hub body, and at least a proximal end of the release member is received in a second chamber defined in part by the coupling element and in part by the sealing element. The cannula module can be pre-assembled for subsequent attachment to the medicament cartridge to form the packaging assembly.

The cannula module may further comprise a crimp fitting for attaching the cannula module to the medicament cartridge.

Preferred and/or optional features of each aspect of the invention may be used, alone or in appropriate combination, in the other aspects also.

BRIEF DESCRIPTION OF THE DRAWINGS

Embodiments of the present invention will now be described, by way of example only, with reference to the accompanying drawings, in which like reference numerals are used for like features, and in which.

Figure 1:
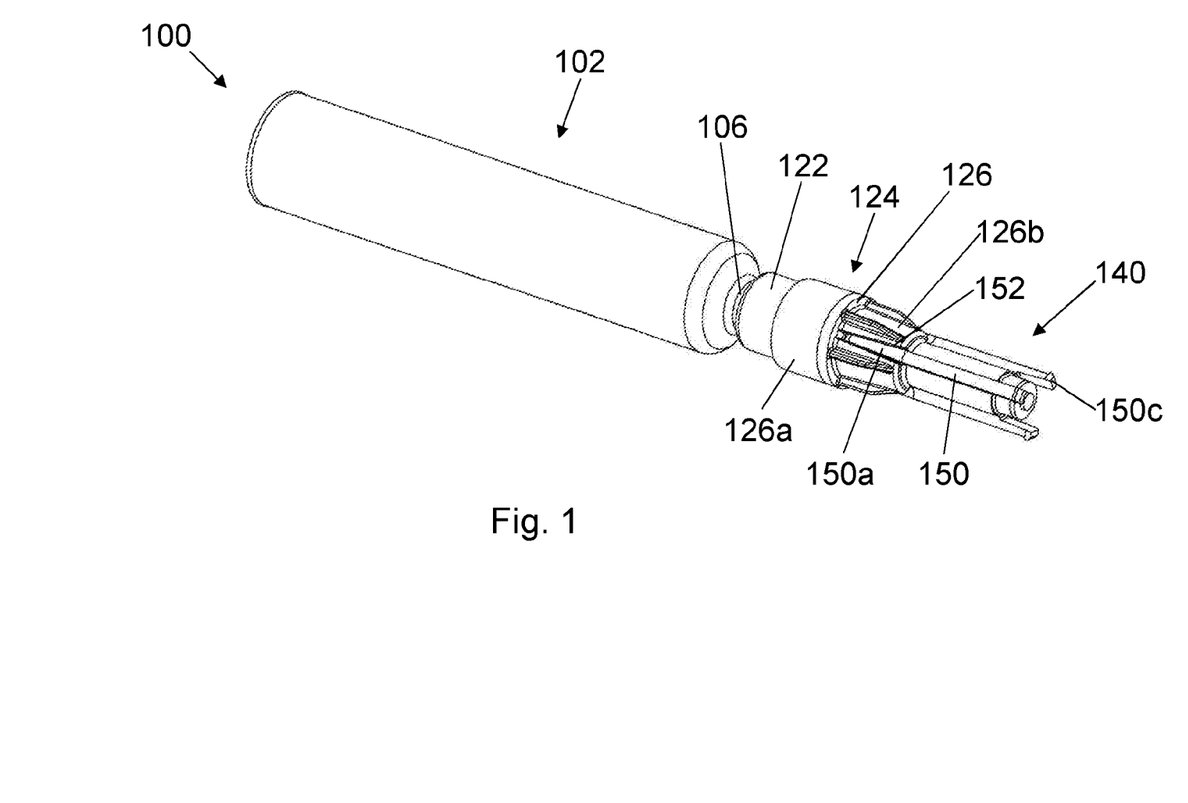
FIG. 1 shows a medicament packaging assembly according to the invention.
Figure 2:
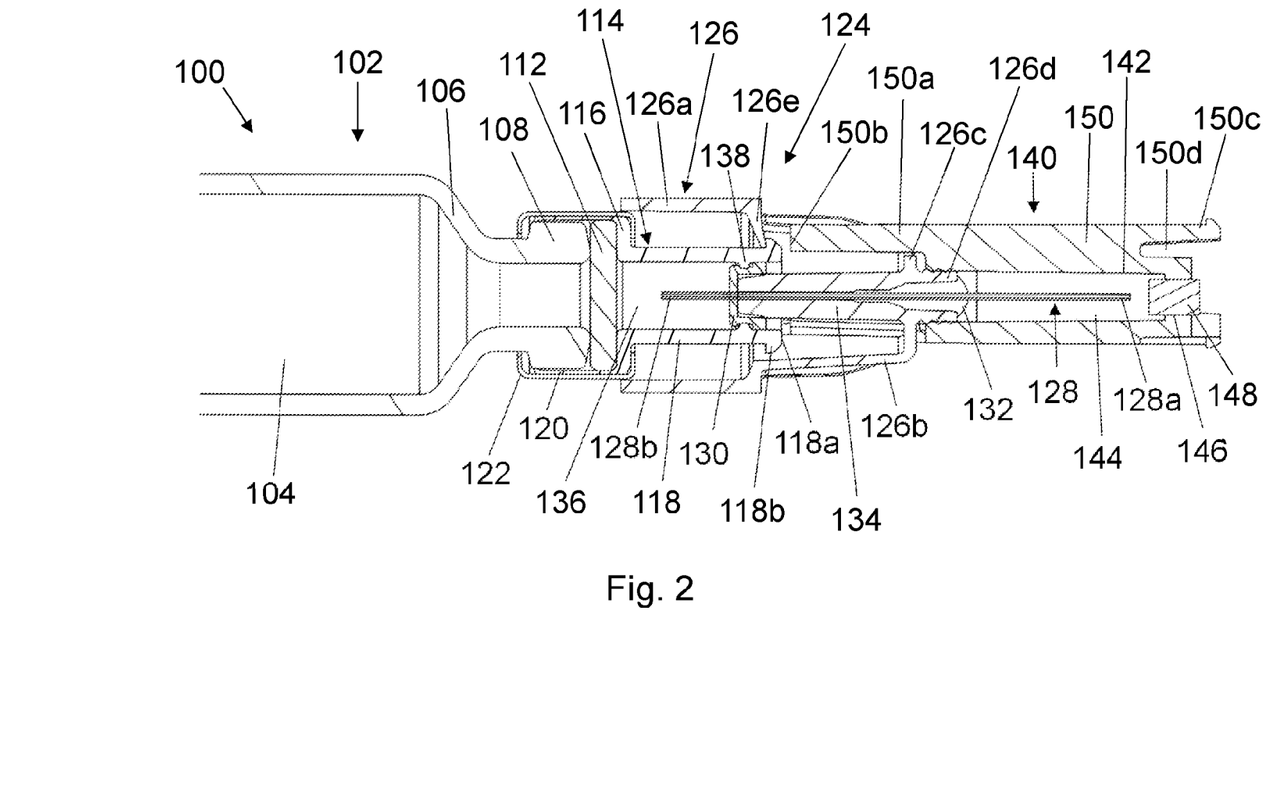
FIG. 2 is a cross-sectional view of the packaging assembly of FIG. 1 when in a starting configuration.

Throughout this specification, the term "distal" and related terms are used to refer to the end of the packaging assembly or device that is closest to the injection site in use (i.e. to the right in FIGS. 1 and 2), and the term "proximal" and related terms are used to refer to the opposite end of the packaging assembly or device (i.e. to the left in FIGS. 1 and 2).

DESCRIPTION OF THE PREFERRED EMBODIMENTS

Figure 3:
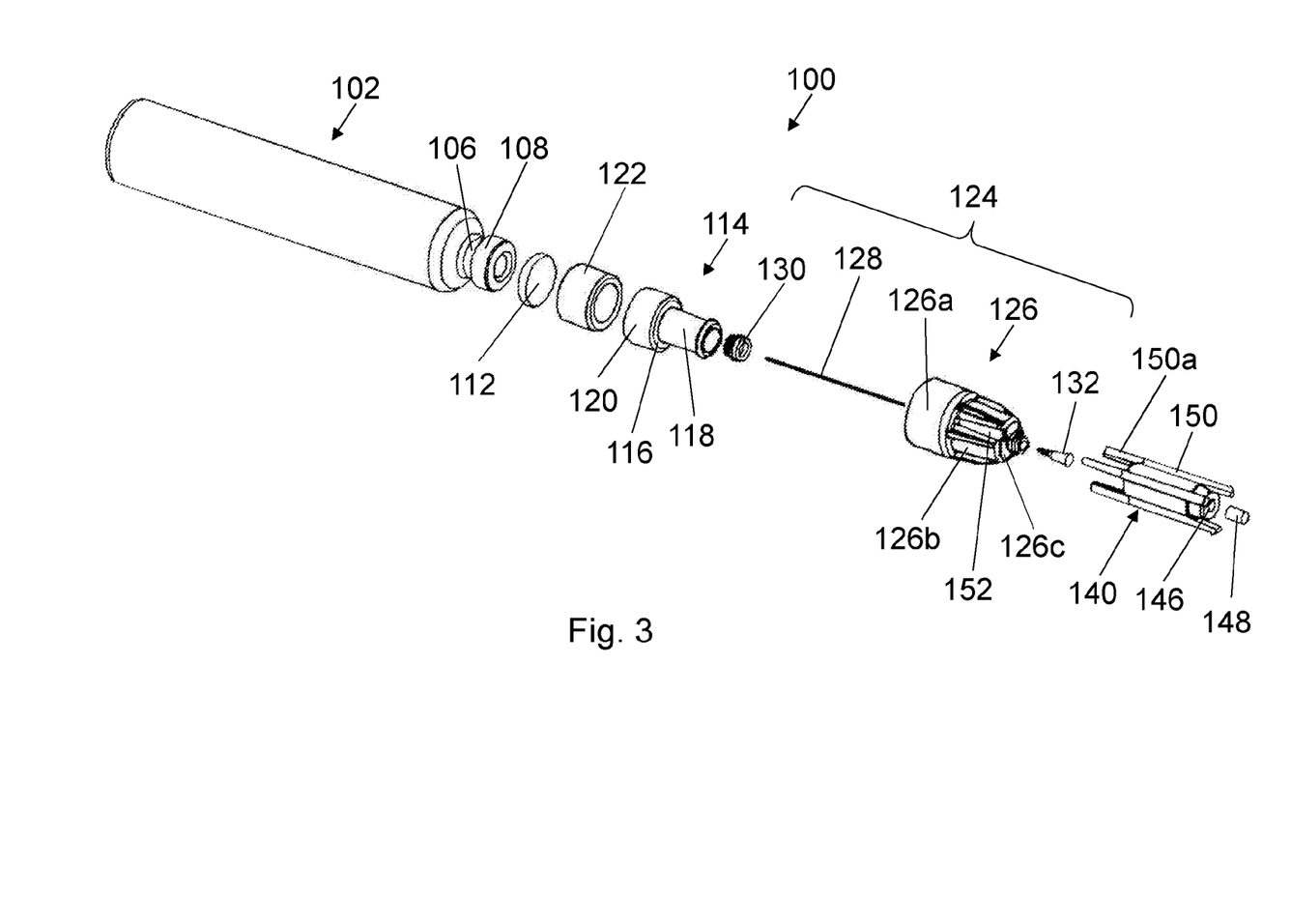
FIG. 3 is an exploded view of the packaging assembly of FIG. 1.

FIGS. 1, 2 and 3 show a medicament packaging assembly 100 according to a first embodiment of the invention. The packaging assembly 100 is suitable for installation in a medicament delivery device 200, which is shown in component form in FIG. 4 and in an assembled state in FIG. 5.

Referring first to FIGS. 1 to 3, the packaging assembly 100 includes a cartridge 102 having a medicament chamber 104 for containing a medicament. The cartridge 102 is generally tubular and has a reduced-diameter neck 106 at its distal end. As can be seen most clearly in FIGS. 2 and 3, an annular collar 108 extends around the neck 106. A piston member comprising a stopper or bung 110 (not shown in FIGS. 1 to 3, see FIGS. 4 and 5) is inserted into the proximal end of cartridge to close the proximal end of the medicament chamber 104.

Referring again to FIGS. 2 and 3, the distal end of the cartridge 102 is closed by a sealing element in the form of a disc-shaped elastomeric septum 112. The septum 112 is clamped against the distal end face of the cartridge 102 by a coupling element 114. The coupling element 114 includes a ring-shaped annular clamping portion 116 that bears against the septum 112, leaving a central part of the septum 112 uncovered by the coupling element 114. A tubular throat 118 extends distally from the clamping portion 116 to provide an engagement portion of the coupling element 114. The throat 118 has a smaller diameter than the clamping portion 116. In this embodiment, a tubular skirt 120 extends proximally from the clamping portion 116, with the collar 108 of the cartridge 102 and the septum 112 being received in the skirt 120. The skirt 120 helps to centre the septum 112 and the coupling element 114 with respect to the cartridge 102 during assembly of the packaging assembly 100. In other embodiments the skirt 120 may be omitted.

The coupling element 114 is attached to the cartridge 102 by a crimp fitting, which in this embodiment comprises a crimp ring 122, preferably formed of a ductile metal such as aluminium. During assembly, the tubular crimp ring 122 is mounted over the skirt 120 and the clamping portion 116 of the coupling element 114 and the ends of the ring 122 are bent inwardly around the proximal side of the collar 108 and the distal side of the clamping portion 116, as can be seen most clearly in FIG. 2. With the crimp ring 122 in place, the clamping portion 116 of the coupling element 114 applies a clamping force to the septum 112 to seal the septum 112 against the distal end of the cartridge 102.

The coupling element 114 cooperates with a hub subassembly 124. The hub subassembly 124 comprises a hub body 126, a cannula in the form of a double-ended hypodermic needle 128, an elastomeric sealing cap 130 for forming a seal between the hub body 126 and the coupling element 114, and a cannula seal 132 for forming a seal between the hub body 126 and the needle 128.

The hub body 126 comprises a generally tubular proximal part 126a and a bell-shaped distal part 126b. The distal end of the hub body 126 has an end face 126c with a central aperture for receiving the needle 128. A tubular cap retaining part 126d surrounds the aperture and extends distally from the end face 126c. The needle 128 is fixed in the aperture by the cannula seal 132, which may for example be of a suitable elastomeric material. A distal end part 128a of the needle 128 projects away from the hub body 126.

A generally tubular boss 134 extends proximally from the end face 126c of the hub body 126, towards the proximal part 126a. The sealing cap 130 fits over the proximal end of the boss 134, and a proximal end part 128b of the needle 128 extends through the cap 130 to project into a chamber 136 defined by the septum 112, the tubular throat 118 of the coupling element 114 and the elastomeric cap 130 of the hub subassembly 124. The sealing cap 130 forms a seal against the inner wall of the throat 118 of the coupling element 114, and is shaped to locate with an inward projection in the form of an annular ridge 138 formed on the inner wall of the throat 118.

The chamber 136 provides an aseptically sealed compartment for the proximal end part 128b of the needle 128. Thus, provided the packaging assembly 100 is assembled in sterile conditions, the proximal end part 128b of the needle 128 remains sterile until the packaging assembly 100 is activated, as will be described below.

Distal movement of the hub subassembly 124 away from the coupling element 114 is prevented by a clip formation. As can be seen most clearly in FIG. 2, the clip formation is formed by a plurality of flexible barbs 126e that extend inwardly from the distal end of the proximal part 126a of the hub body 126 to engage with a collar 118b formed at the distal end of the throat 118 of the coupling element 114. The collar 118b has a ramped distally-facing surface to allow the barbs 126e to pass proximally over the collar 118b during assembly of the packaging assembly 100, and a perpendicular proximally-facing surface to prevent the barbs 126e from passing back over the collar 118b. In this way, the hub subassembly 124 is retained on the coupling element 114 after assembly of the packaging assembly 100.

A cap sleeve member 140 is fitted to the distal end of the packaging assembly 100. The cap sleeve member 140 has a distally-extending bore 142 that defines, in part, a cap chamber 144 for receiving the distal end part 128a of the needle 128. The cap retaining part 126d of the hub body 126 engages with an interference fit in a proximal end of the bore 142, to form a seal between the cap sleeve member 140 and the hub body 126. In an alternative arrangement (not shown), an O-ring seal is provided between the cap sleeve member 140 and the cap retaining part 126d of the hub body 126.

A small-diameter bore 146 extends proximally from the distal end of the cap sleeve member 140 to connect with the distally-extending bore 142. The small-diameter bore 146 is plugged with a cylindrical closure 148 comprising an air-permeable sterile barrier material, such as available under the registered trade marks Tyvek (DuPont, DE, USA) and Vyon (Porvair PLC., Norfolk, UK). The closure 148 allows air to flow into or out of the cap chamber 144 and the release member chamber 136 (through the flow path provided by the cannula 128) to equalise the pressure in the chambers 136, 144. This eliminates pressure gradients across the seals between the septum 112 and the coupling element 114, between the coupling element 144 and the hub body 126, and between the hub body 126 and the cap sleeve member 140, reducing the risk of failure of these seals. The sterile barrier properties of the material of the closure 148 prevent microbial contamination of the cap chamber 144. In some cases (not illustrated), where equalisation of pressure is not required, the small-diameter bore 146 may be omitted so that the cap chamber 144 is closed and sealed by the distal end of the cap sleeve member 140.

The cap chamber 144 therefore provides an aseptically sealed compartment for the distal end part 128a of the needle 128. Again, provided the packaging assembly 100 is assembled in sterile conditions, the distal end part 128a of the needle 128 remains sterile until the packaging assembly 100 is activated, as will be described further below.

The cap sleeve member 140 is provided with a plurality of ribs 150. The ribs 150 extend parallel to the longitudinal axis of the cap sleeve member 140 and are disposed in an equi-angular arrangement around the outside of the cap sleeve member 150. In the illustrated example, three ribs 150 are provided, but fewer or more ribs 150 may be present.

Each rib 150 is extended proximally to form a blocking member or blocking finger 150a. As can be seen most clearly in FIG. 1, each blocking finger 150a is received in a corresponding aperture 152 in the distal part 126b of the hub body 126.

Referring to FIG. 2, with the cap sleeve member 140 in place, the proximal end tip 150b of each blocking finger 150a is positioned to cooperate with the distal end face 118a of the throat 118 of the coupling element 114. Thus movement of the coupling element 114 in a distal direction with respect to the hub subassembly 124 or, equivalently, movement of the hub subassembly 124 in a proximal direction with respect to the coupling element 114 is blocked by abutment between the blocking finger 150a and the coupling element 114. The blocking fingers 150a therefore prevent the packaging assembly 100 from moving out of a starting configuration in which the proximal end of the needle 128 is spaced apart from the septum 112. This arrangement advantageously prevents accidental activation of the packaging assembly 100, for example in the event that the packaging assembly 100 is dropped.

Each rib 150 is also extended distally to form a clip formation 150c. The clip formations 150c are separated from the distal end region of the cap sleeve member 140 by slots 150d, so that the clip formations 150c are flexible. The clip formations 150c are used to couple the packaging assembly 100 to an outer cap of a medicament delivery device 200, as will be explained below.

Once the packaging assembly 100 has been assembled in its starting configuration in a sterile environment, all of the components of the packaging assembly 100 that will come into contact with the medicament in use, as well as the medicament in the medicament chamber 104 and the distal end part 128a of the needle 128 (which passes into the injection site) remain sterile.

One convenient way of pre-assembling the packaging assembly comprises first attaching the septum 112, the crimp ring 122, the coupling element 114 and the cap sleeve member 140 to the hub subassembly 124 and sterilising these components to from a sterile cannula module. The cannula module can then be secured to the distal end of the cartridge 102 by crimping the crimp ring 122.

The packaging assembly 100 as a whole can then be installed in a medicament delivery device 200. Advantageously, the maximum diameter of the packaging assembly 100 corresponds to the diameter of the cartridge 102, with the cap sleeve member 140, the hub body 126 and the coupling element 114 all having smaller diameters than the diameter of the cartridge 102. In this way, the packaging assembly 100 can be inserted into a device housing from the proximal end of the housing.

Figure 4:
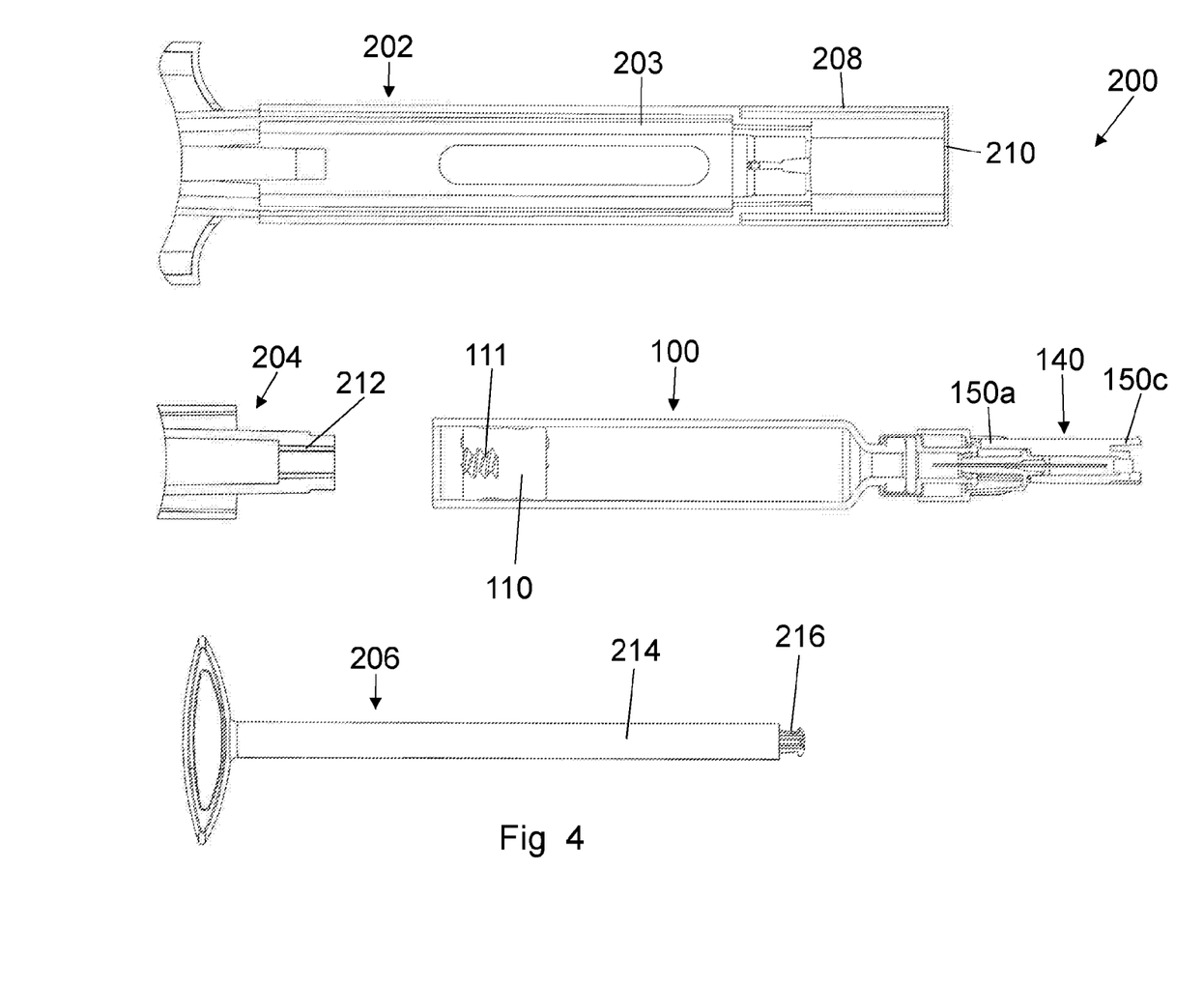
FIG. 4 shows cross-sectional views of components of a medicament delivery device according to the invention, including the packaging assembly of FIG. 1.

FIG. 4 shows the packaging assembly 100 in its starting configuration together with a device housing 202, a proximal end fitting 204 and a plunger 206. In this example, the device 200 comprises a manually-operated syringe.

The housing 202 has a generally cylindrical interior space 203 to accept the packaging assembly 100. At a distal end of the housing 202, an outer cap 208 is provided. The outer cap 208 engages with the housing 202 and is removable in use of the device 200.

Figure 5:
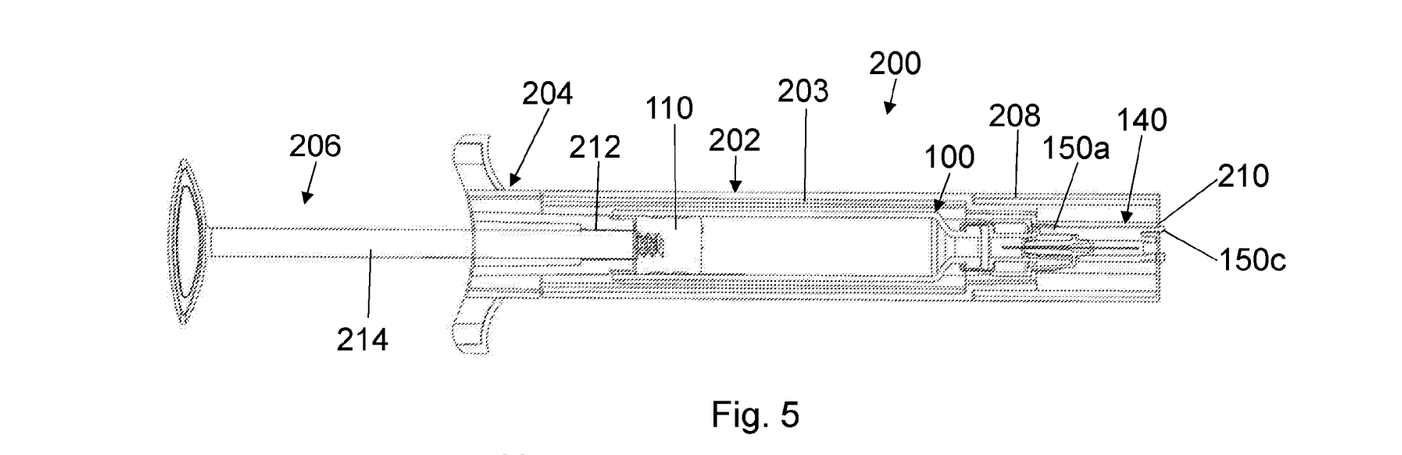
FIG. 5 is a cross-sectional view of the assembled medicament delivery device of FIG. 4.

Referring additionally to FIG. 5, the device 200 can be assembled by inserting the packaging assembly 100 through the proximal end opening of the interior space 203 of the housing 202 and pushing the assembly 100 distally until the clip formations 150c of the cap sleeve member 140 engage in corresponding slots 210 provided in the distal end face of the outer cap 208. In the illustrated embodiment, the outer cap 208 is engaged with the housing 202 before the packaging assembly 100 is inserted, but equivalently the packaging assembly 100 could be inserted to the housing 202 and held in place while the outer cap 208 is subsequently attached.

In either case, a distally-directed force (i.e. a direct force or a reaction force) acts on the packaging assembly 100 to engage the cap sleeve member 140 with the outer cap 208. The presence of the blocking formations 150a prevents the packaging assembly 100 from moving out of its starting configuration during the insertion process.

The proximal end fitting 204 clips into the proximal end of the housing 202 to retain the packaging assembly 100 in the housing 202. The proximal end fitting 204 also provides a guide bore 212 for an elongate plunger rod 214 of the plunger 206. A distal tip 216 of the plunger rod 214 is formed to engage with a corresponding recess 111 in the proximal side of the bung 110.

Figure 6:
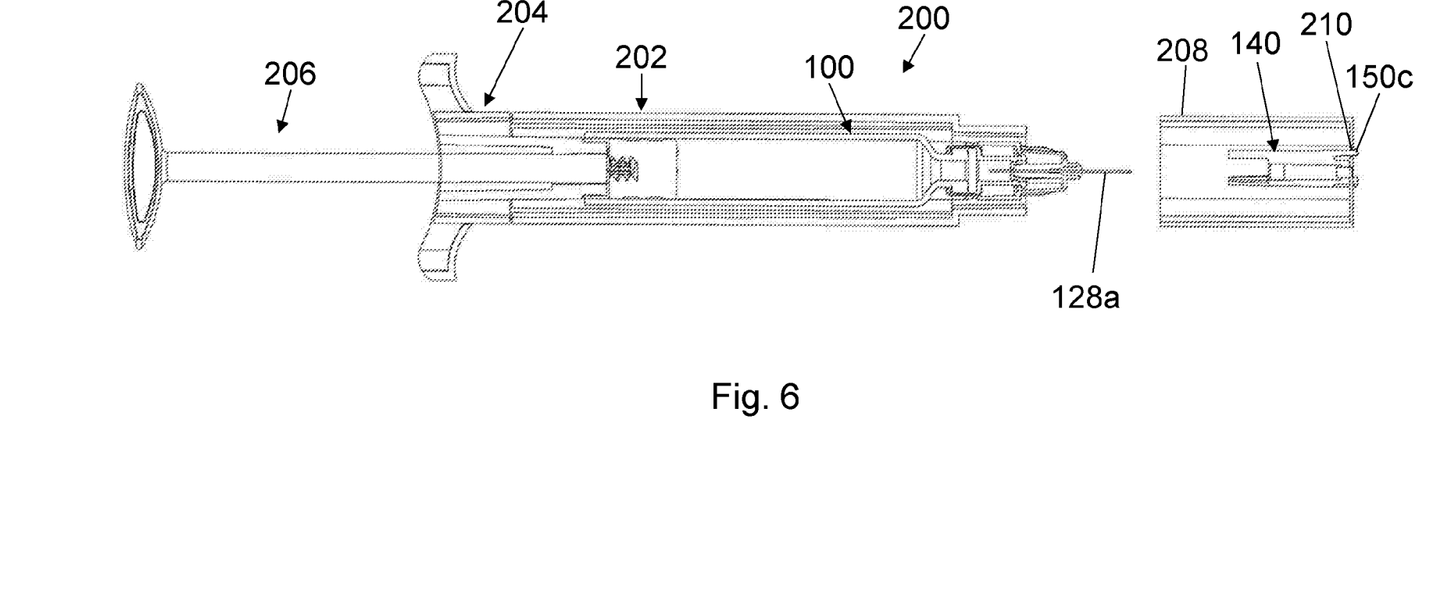
FIG. 6 is a cross-sectional view of the delivery device of FIG. 4 after removal of a cap.
Figure 7:
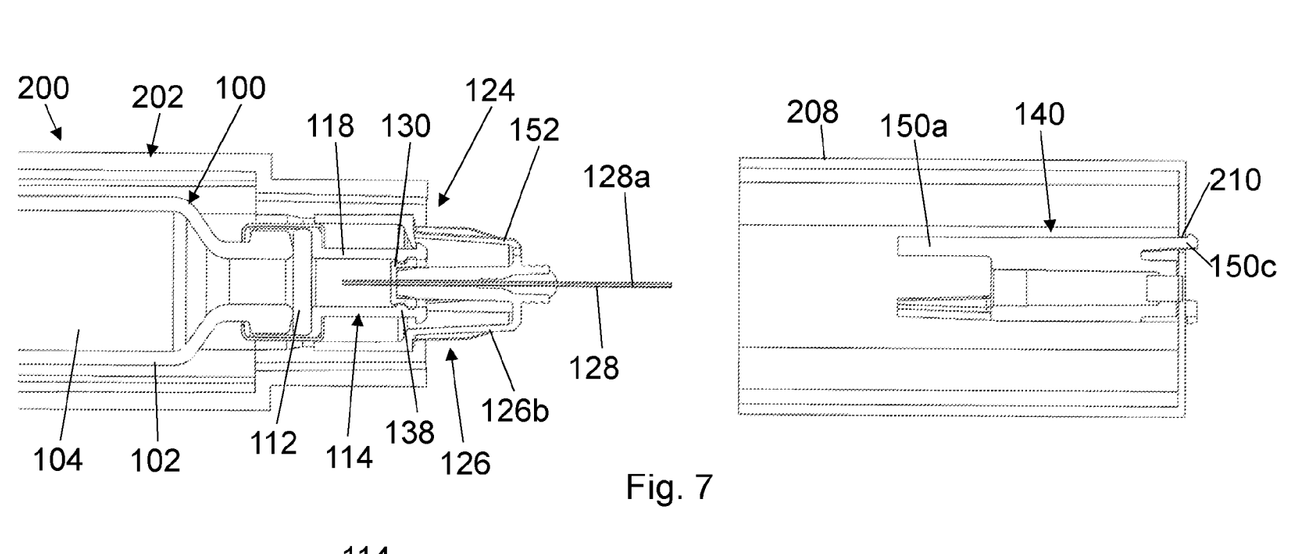
FIG. 7 is a cross-sectional view of part of the delivery device of FIG. 4 after removal of the cap.

To prepare the device 200 for use, the outer cap 208 can be removed from the housing 202, as shown in FIG. 6 and in greater detail in FIG. 7. Because the cap sleeve member 140 is engaged with the outer cap 208, the cap sleeve member 140 is removed along with the outer cap 208, exposing the distal end part 128a of the needle 128 and withdrawing the blocking formations 150a from the apertures 152 in the hub body 126 in a linear movement.

Figure 8:
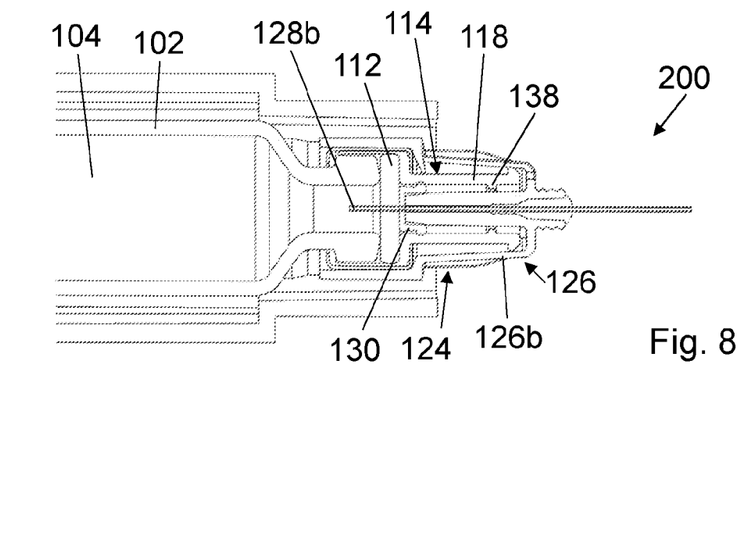
FIG. 8 is an enlarged cross-sectional view of part of the delivery device of FIG. 4 when the packaging assembly has been switched to an activated configuration.

To operate the device 200, the plunger 206 is pushed distally with respect to the housing 202. The force initially applied to the packaging assembly 100, via the plunger rod 214 and the bung 110, causes the cartridge 102, the septum 112 and the coupling element 114 to move distally with respect to the hub subassembly 124, moving the throat 118 of the coupling element 114 into the distal part 126b of the hub body 126 as shown in FIG. 8.

The elastomeric sealing cap 130 disengages from the ridge 138, and the proximal end part 128b of the needle 128 pierces the septum 112 to connect the needle 128 to the medicament chamber 104. The packaging assembly 100, and hence the device, is now in an activated state in which a flow path from the medicament chamber 104 to the distal end of the needle 128 has been established.

Delivery of the medicament through the needle 128 can then take place by further displacement of the plunger 206 in the distal direction.

Figure 9:
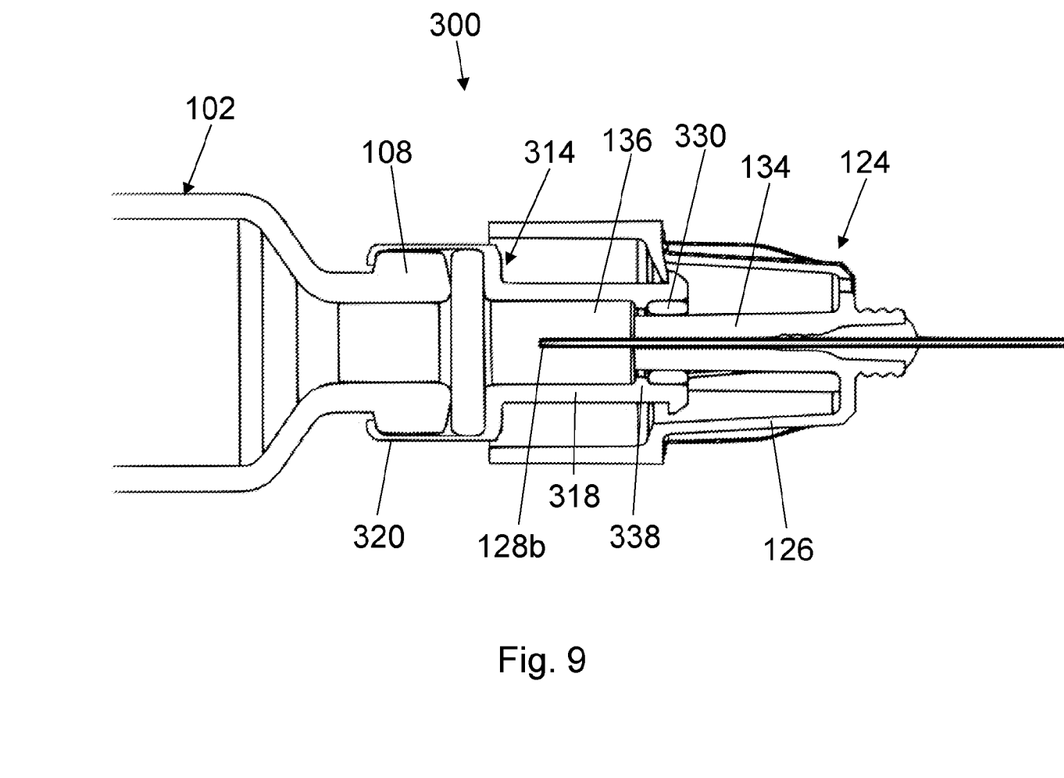
FIG. 9 is a cross-sectional view of part of another packaging assembly according to the invention.

FIG. 9 shows part of a packaging assembly 300 according to another embodiment of the invention, which differs from the packaging assembly 100 of FIGS. 1 to 8 in only two respects which will be described below. The structure and operation of the packaging assembly 300 of FIG. 9 is otherwise identical to the previous embodiment. The cap sleeve member of the packaging assembly 300 is not shown in FIG. 9.

In the packaging assembly 300 of FIG. 9, the coupling element 314 is attached to the cartridge 102 by way of a crimp fitting that is formed integrally with the coupling element 314. In particular, the proximal end of the skirt 320 is deformed during assembly to clasp around the collar 108. In this embodiment, the coupling element 314 may be of a suitable ductile material such as aluminium.

Also, instead of an elastomeric sealing cap, in this embodiment an elastomeric O-ring seal 330 is used to provide the aseptic seal between the boss 134 of the hub body 126 and the throat 318 of the coupling element 314. The O-ring seal 330 is kept in place by the ridge 338 on the interior wall of the throat 318. It will be appreciated that other arrangements are possible and that any suitable seal between the coupling element 314 and the hub subassembly to seal the proximal part 128b of the needle 128 in the chamber 136.

Figure 10:
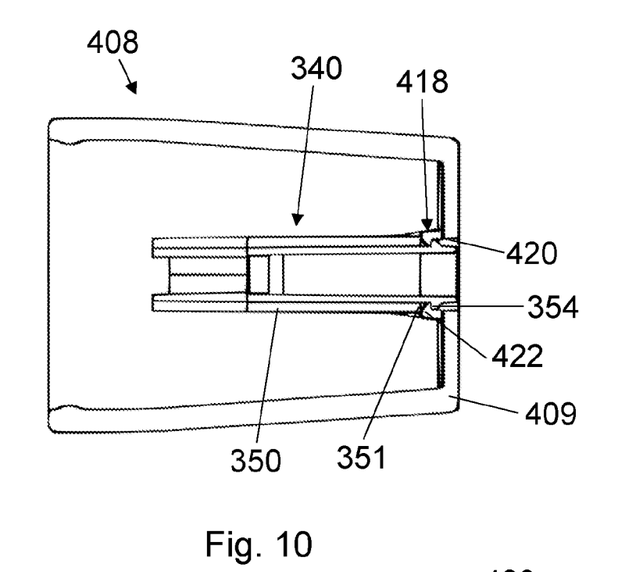
FIG. 10 is a cross-sectional view of a cap member and an outer cap for use in a variant of the invention.
Figure 11:
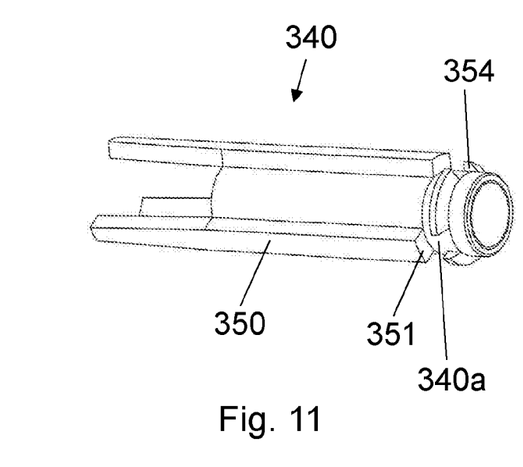
FIG. 11 is a perspective view of the cap member of FIG. 10.
Figure 12:
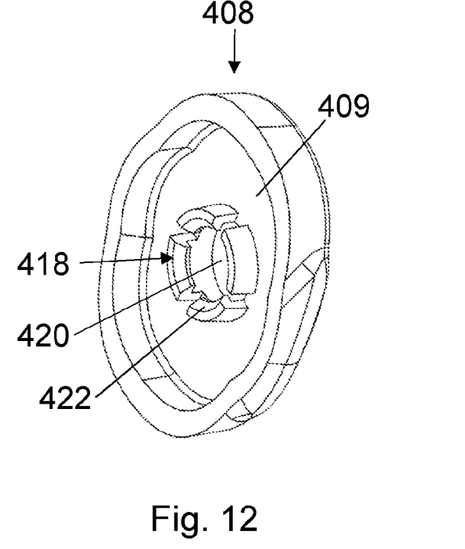
FIG. 12 is a cut-away perspective view of part of the outer cap of FIG. 10.

FIGS. 10 to 12 show variants of an outer cap 408 and a cap sleeve member 340 that could be used in variants of the packaging assemblies 100, 300 of the previously-described embodiments. The outer cap 408 and cap sleeve member 340 are similar to those described above and only the differences are described in detail. FIG. 10 shows the cap sleeve member 340 engaged with the outer cap 408. FIG. 11 shows the cap sleeve member 340 in isolation, and FIG. 12 is a cut-away view of the distal end of the outer cap 408 to show a proximally-facing side of the distal end wall 409 of the outer cap member 408.

In this case, the cap sleeve member 340 is provided with arcuate ramp formations 354 that extend radially outwardly from a distal end portion 340a of the cap sleeve member 340. The ribs 350 do not extend into the distal end portion 340a of the cap sleeve member 340. Instead, the distal end surface of each rib 350 provides a stop 351.

The outer cap 408 is provided with clip formations 418 arranged around the perimeter of a circular aperture 420 in the distal end wall 409. Each clip formation 418 extends proximally from the distal end wall 409 of the outer cap 408 and includes a ramped, inwardly-facing head 422 at its proximal end.

To engage the cap sleeve member 340 with the outer cap 408, the distal end of the cap sleeve member 340 is pushed into the aperture 420 so that the clip formations 418 of the outer cap 408 flex outwardly and pass over the ramp formations 354 of the cap sleeve member 340. The clip formations 418 engage with the proximal sides of the ramp formations 354 as shown in FIG. 10. Further distal movement of the cap sleeve member 340 with respect to the outer cap 408 is limited by abutment of the stops 351 with the clip formations 418.

Because the clip formations 418 of the outer cap are arranged around the circular periphery of the aperture 420, the cap sleeve member 340 can be engaged with the outer cap 408 irrespective of the relative angular orientation of the components about the longitudinal axis of the cap sleeve member 340.

Although not illustrated, other means for engaging the cap sleeve member and the outer cap are possible. Preferably, both the cap sleeve member and the outer cap are provided with complementary engagement formations to allow engagement of the cap sleeve member with the outer cap when the cap sleeve member is inserted into the outer cap. At least one of the engagement formations may be arranged to flex in order to engage the cap sleeve member with the outer cap. Examples of suitable engagement formations include clips, ramp formations, projections, recesses, apertures, slots and so on.

Although FIGS. 4 to 8 illustrate a packaging assembly 100 in use in a delivery device 200 comprising a manual syringe, the packaging assembly 100 can be used in a wide variety of different delivery devices. In particular, the packaging assembly 100 can be used in auto-injector devices in which one or more of the steps of needle insertion into an injection site, delivery of the medicament, retraction of the needle and shielding the needle may be driven by an energy source such as a spring.

Figure 13A:
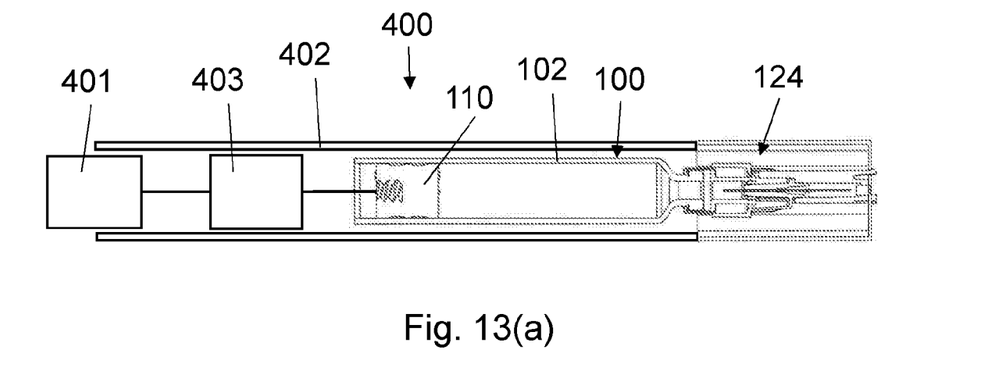
FIGS. 13(a), (b) and (c) show schematic cross-sectional views of further delivery devices according to the invention.

For example, FIG. 13(a) shows the packaging assembly 100 installed in an auto-injector device 400 having a trigger mechanism 401 and a drive mechanism 403. In this case, the trigger mechanism 401 is operable by a user to cause the drive mechanism 403 to move the stopper 110 in the distal direction with respect to the housing 402, for example using a drive spring. In this case, switching of the packaging assembly 100 from the starting configuration to the activated configuration occurs during an initial phase of operation of the drive mechanism 403 in which distal movement of the bung 110 also causes distal movement of the cartridge 102 with respect to the housing 402 and the hub subassembly 124. The drive mechanism 403 may also act as an insertion mechanism by driving the whole packaging assembly 100 in the distal direction before delivery of the medicament. Suitable trigger mechanisms and drive mechanisms will be familiar to those skilled in the art.

Figure 13B:
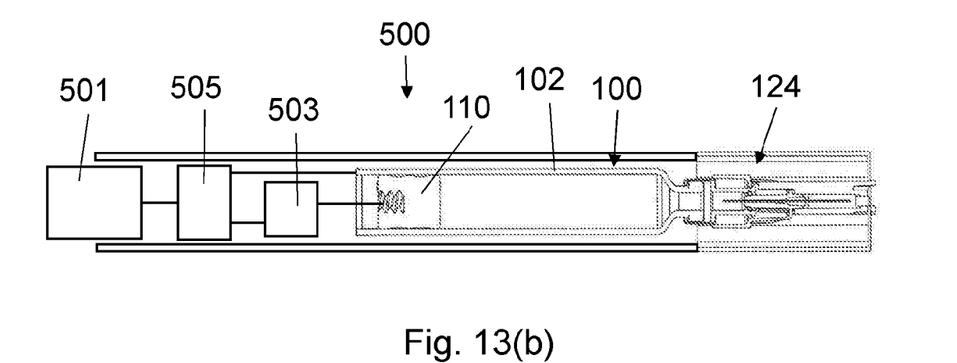

FIG. 13(b) shows the packaging assembly 100 installed in another auto-injector device 500. In this case, the device 500 has a trigger mechanism 501 that operates an activating mechanism 505 which, in turn operates a drive mechanism 503. Operation of the trigger mechanism 501 by the user causes the activating mechanism 505 to displace the cartridge 102 in the distal direction with respect to the hub subassembly 124, switching the packaging assembly 100 from the starting configuration to the activated configuration. Subsequently, the drive mechanism 503 displaces the bung 110 in the distal direction with respect to the cartridge 102 to deliver the medicament. Optionally, either the activating mechanism 505 or the drive mechanism 503 could be arranged also to cause insertion of the needle. Again, suitable mechanisms will be familiar to those skilled in the art.

Figure 13C:
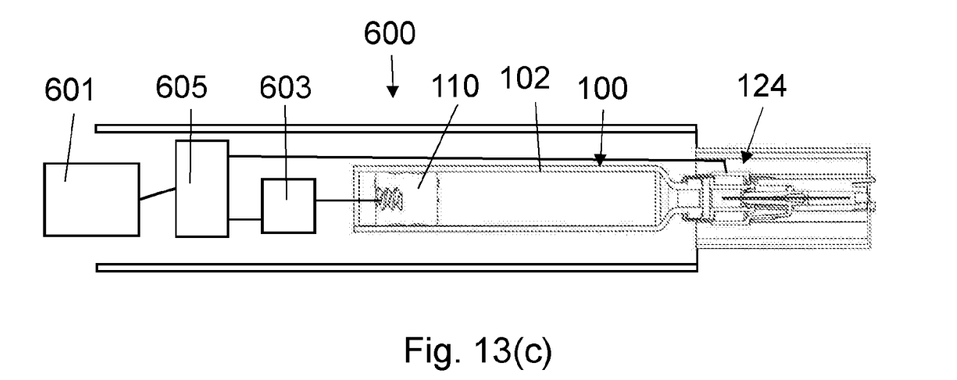

FIG. 13(c) shows the packaging assembly 100 installed in another auto-injector device 600. This device 600 also has a trigger mechanism 601 that operates an activating mechanism 605 which, in turn operates a drive mechanism 603, but in this case operation of the trigger mechanism 601 by the user causes the activating mechanism 605 to displace the hub subassembly 124 proximal direction with respect to the cartridge 102, switching the packaging assembly 100 from the starting configuration to the activated configuration. Subsequently, the drive mechanism 603 displaces the bung 110 in the distal direction with respect to the cartridge 102 to deliver the medicament. Optionally, either the activating mechanism 605 or the drive mechanism 603 could be arranged also to cause insertion of the needle. Again, suitable mechanisms will be familiar to those skilled in the art.

In the examples of FIG. 13, the trigger mechanism 601 may be activated by a button disposed at a proximal end of the housing or by other means such as by a slider, a skin-contact sensor, telescoping housing parts, and so on, as will be familiar to those skilled in the art.

Further variations and modifications may be contemplated. For example, in the illustrated examples, the cannula is a double-ended needle, and the proximal end part of the needle acts as a piercing member for the septum. However, a single-ended needle could be provided for delivery of the medicament, with a separate piercing member being formed integrally with the hub body or as a separate component. It is also conceivable that, instead of a septum, the distal end of the cartridge could be sealed by a valve, rupturable membrane or other sealing device. In such cases the sealing element may be released by a suitable release member, which need not be a piercing member but could instead be arranged to open a valve, rupture a membrane and so on.

The cannula need not be a needle, but could instead be a flexible cannula or other suitable infusion or injection device. The cannula need not be mounted directly in the hub body but could instead be connected to the hub body by a flexible tube or the like.

Further modifications and variations not explicitly described above are also possible without departing from the scope of the invention as defined in the appended claims.

The invention claimed is:

1. A medicament packaging assembly for installation in a medicament delivery device, the packaging assembly comprising:
    a cartridge having a medicament chamber for containing a medicament; a seal for sealing a distal end of the medicament chamber; a seal release; a cannula for delivery of the medicament; and a removable cap member;
    wherein the cap member is arranged for engagement with an outer cap of the device and comprises at least one blocking finger for limiting movement of the cartridge in a distal direction toward the seal release when the cap member is in place, thereby to keep the packaging assembly in a starting configuration when the cap member is in place;
    wherein, after removal of the cap member, the packaging assembly is configured to undergo relative movement between the seal release and the cartridge from the starting configuration in which the seal release is spaced from the seal to an activated configuration in which the seal release cooperates with the seal to connect the medicament chamber to the cannula;
    the packaging assembly further comprising:
    a first chamber defined in part by the cap member and arranged for receiving the cannula such that at least a distal end of the cannula is sealed in the first chamber when the cap member is in place; and
    a second chamber defined in part by the seal and arranged for receiving the seal release such that at least a proximal end of the seal release is sealed in the second chamber when the packaging assembly is in the starting configuration;
    wherein the packaging assembly can be pre-assembled in the starting configuration for subsequent installation in the device and the cap member is arranged to engage with the outer cap of the device upon application of a distally-directed force to the packaging assembly, the at least one blocking finger being arranged to keep the packaging assembly in the starting configuration in which the seal release is spaced from the seal during application of the distally-directed force.

2. A packaging assembly according to claim 1, wherein the cap member comprises one or more clip formations for engagement with the outer cap.

3. A packaging assembly according to claim 1, wherein the cap member has a diameter equal to or less than the diameter of the cartridge.

4. A packaging assembly according to claim 3, wherein the maximum diameter of the packaging assembly is equal to the diameter of the cartridge.

5. A packaging assembly according to claim 1, wherein the cap member comprises a vent for venting the first chamber, the vent comprising an air permeable sterile barrier material.

6. A packaging assembly according to claim 1, further comprising a hub subassembly including a hub body, the cannula and the seal release.

7. A packaging assembly according to claim 6, further comprising a coupling element attached to the cartridge, wherein the second chamber is defined in part by the coupling element and wherein an aseptic seal is formed between the hub body and the coupling element to seal the second chamber at least when the packaging assembly is in the starting configuration.

8. A packaging assembly according to claim 7, wherein the hub body comprises a proximally-projecting boss for the seal release and wherein the second chamber is defined in part by a distally-projecting tubular member of the coupling element, the tubular member being arranged to receive the boss and the aseptic seal being formed between the tubular member and the boss at least when the packaging assembly is in the starting configuration.

9. A packaging assembly according to claim 8, in which the hub subassembly comprises an elastomeric cap mounted on the boss, wherein the seal release projects through the elastomeric cap and wherein the elastomeric cap forms the aseptic seal between the tubular member and the boss.

10. A packaging assembly according to claim 7, wherein the cap member is engageable with the hub body and wherein the at least one blocking finger extends proximally from the cap member to cooperate with the coupling element to limit relative movement between the seal release and the cartridge.

11. A packaging assembly according to claim 10, wherein a tip of the at least one blocking finger is arranged to abut the coupling element to limit relative movement between the seal release and the cartridge.

12. A packaging assembly according to claim 7, wherein the at least one blocking finger extends through a corresponding aperture in the hub body.

13. A packaging assembly according to claim 7, wherein the coupling element is attached to a collar of the cartridge by a crimp fitting.

14. A packaging assembly according to claim 13, wherein the coupling element comprises a skirt that extends over the collar to form the crimp fitting.

15. A packaging assembly according to claim 7, wherein the seal comprises a septum, and wherein the coupling element clamps the septum against a distal end of the cartridge.

16. A packaging assembly according to claim 7, comprising a clip formation arranged to allow engagement of the hub subassembly with the coupling element during assembly of the packaging assembly and to prevent subsequent disengagement of the hub subassembly from the coupling element.

17. A packaging assembly according to claim 16, wherein the hub body comprises one or more inwardly-extending clips that cooperate with a collar of the coupling element to provide the clip formation.

18. A packaging assembly according to claim 1, wherein the release comprises a tubular element arranged to pierce the seal upon switching of the packaging assembly into the activated configuration.

19. A packaging assembly according to claim 18, wherein the cannula comprises a distal part of a needle and the seal release comprises a proximal part of the needle.

20. A method for assembling a medicament delivery device, comprising:
providing a medicament delivery device;
assembling a medicament packaging assembly according to claim 1; and
inserting the assembled packaging assembly into the medicament delivery device.

21. A method according to claim 20, wherein the medicament delivery device further comprises a removable outer cap, and
the method further comprising engaging the cap member of the packaging assembly with the removable outer cap of the delivery device.

22. A method according to claim 20, wherein the step of inserting the packaging assembly comprises applying a distally-directed force to the packaging assembly to engage the cap member with the outer cap.

23. A medicament delivery device comprising:
a medicament packaging assembly according to claim 6;
a housing for receiving the medicament packaging assembly according to claim 6;
the removable outer cap provided on a distal end of the housing, the outer cap being engageable with the cap member of the packaging assembly when the packaging assembly is inserted into the housing; and
an activation driver operable to cause relative movement between the cartridge and the hub subassembly, thereby to switch the packaging assembly from the starting configuration to the activated configuration to allow delivery of the medicament through the cannula.

24. A cannula module for use in a packaging assembly in which a medicament is contained in a medicament chamber of a cartridge, the cannula module comprising:
a seal for sealing an end of the medicament chamber, a coupling element, a cap sleeve member and a hub subassembly, the hub subassembly comprising a hub body, a cannula for delivery of the medicament, and a seal release, the cap sleeve member comprising at least one blocking finger;
wherein, when the cap sleeve member is in place, the cap sleeve member maintains the cannula in a starting configuration in which a distal end of the cannula is received in a first chamber defined in part by the cap sleeve member and in part by the hub body and a proximal end of the seal release is received in a second chamber defined in part by the coupling element and in part by the seal;
wherein, when the cap sleeve member is in place, relative movement between the seal release and the seal is limited so that the seal release is spaced apart from the seal;
wherein, after removal of the cap sleeve member, the medicament chamber is moveable in a distal direction toward the seal release so that the seal release cooperates with the seal to connect the medicament chamber to the cannula;
wherein the cannula module can be pre-assembled for subsequent attachment to the medicament cartridge to form the packaging assembly; and
wherein the at least one blocking finger is arranged to keep the packaging assembly in the starting configuration in which the seal release is spaced from the seal during application of a distally-directed force to the packaging assembly.

25. A cannula module according to claim 24, further comprising a crimp fitting for attaching the cannula module to the medicament cartridge.

26. A cannula module according to claim 24, wherein the cap sleeve member comprises one or more ribs which extend proximally to form one or more blocking members and distally to form one or more clips.

* * * * *